VARIETY OF WHITE ASH TREE
Filed June 27, 1974 2 Sheets-Sheet 1
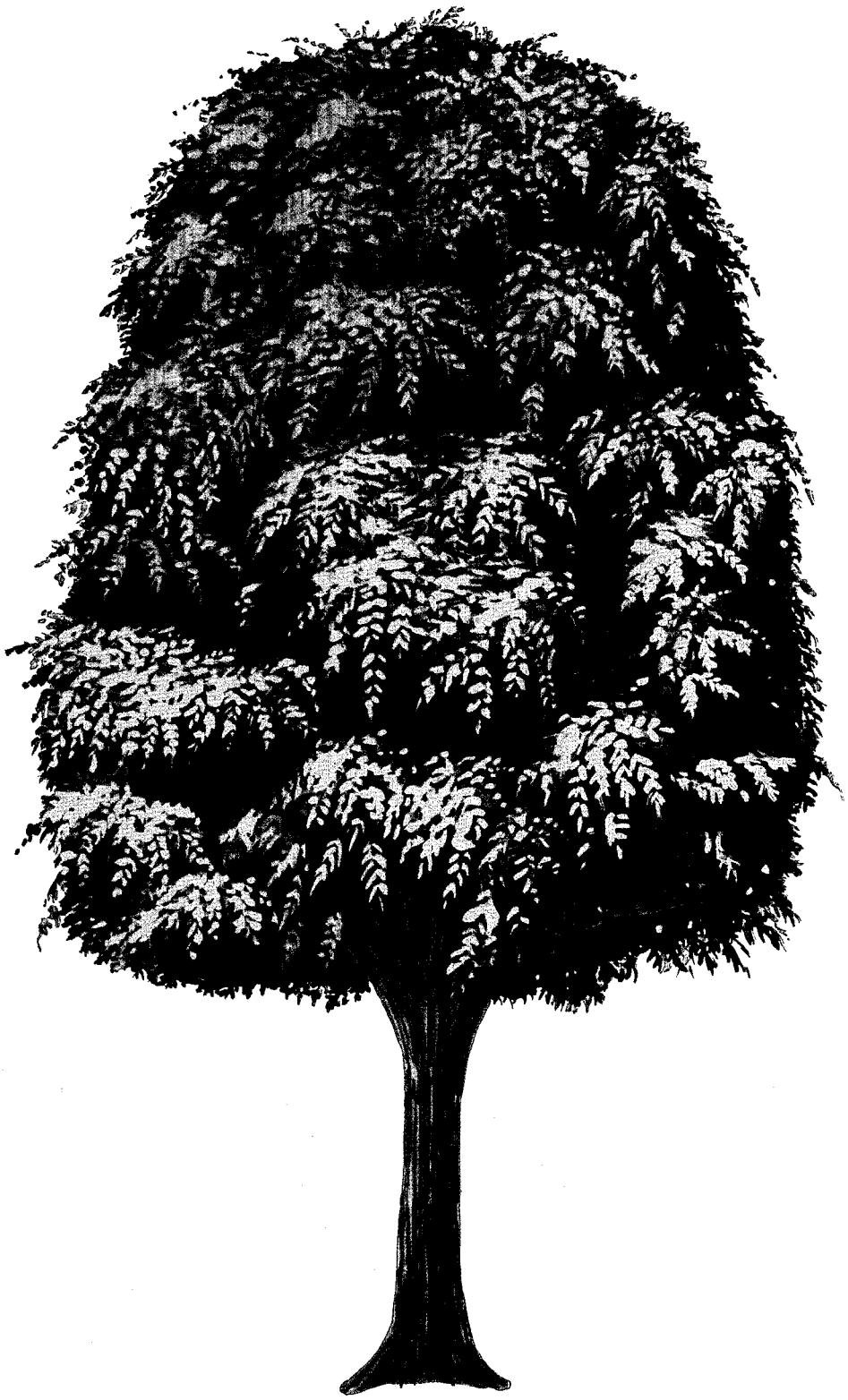

VARIETY OF WHITE ASH TREE
Filed June 27, 1974 2 Sheets-Sheet 2
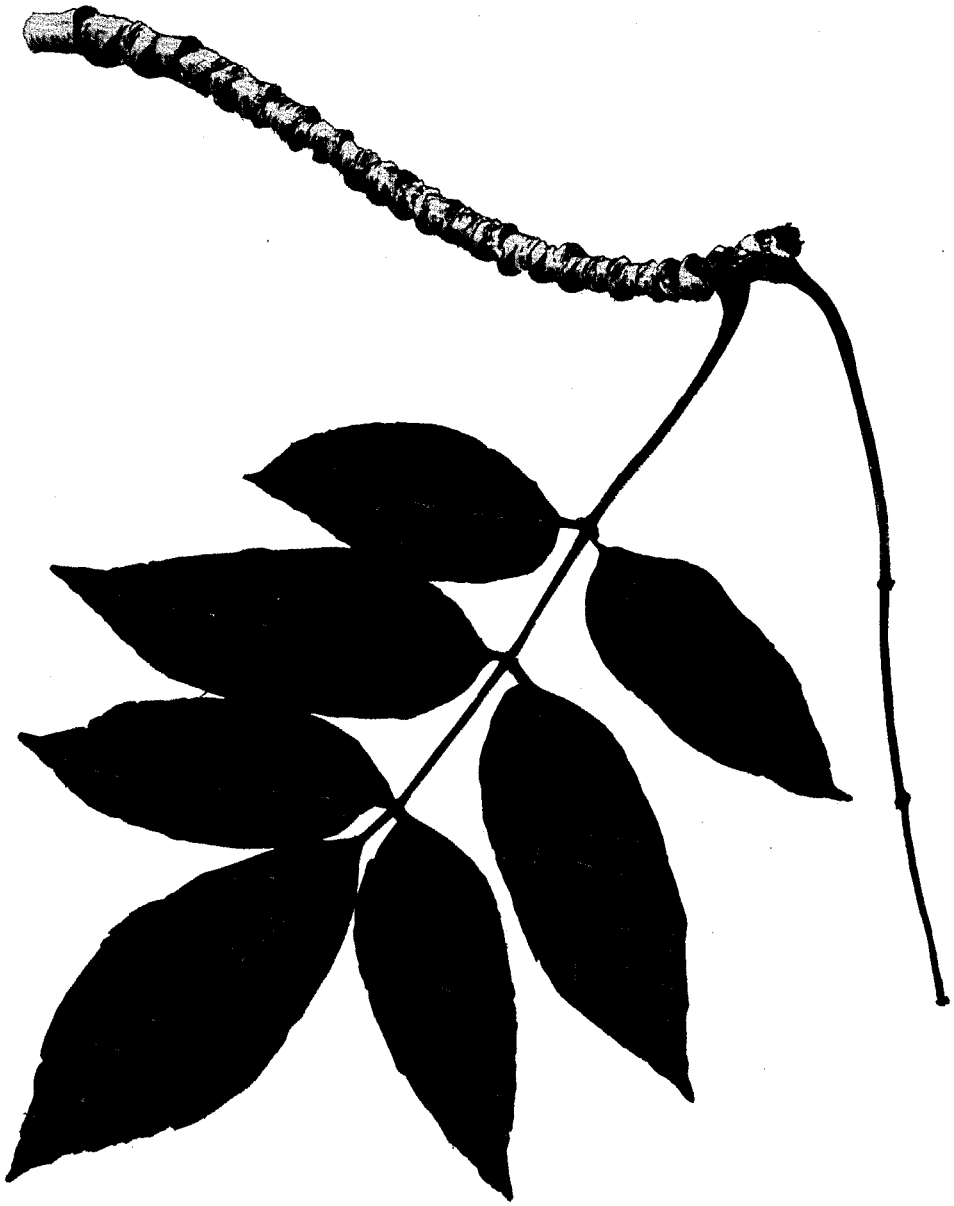

United States Patent

Plant Pat. 3,769
Patented Aug. 26, 1975

3,769

VARIETY OF WHITE ASH TREE

Willet N. Wandell, Rte. 3, Myra Station Road,
Urbana, Ill. 61801

Filed June 27, 1974, Ser. No. 483,875
Int. Cl. A01h 5/12
U.S. Cl. Plt.—51 1 Claim The present invention relates to a new and distinct variety of white ash discovered on a private farmstead in Urbana Township, Champaign County, Ill. The new variety developed from an unnamed seedling of the species *Fraxinus americana.*

The new variety of white ash is characterized by its broad upright spreading shape and fine texture of foliage. The leaves are smaller in size than other white ash of the area, and the rachis upon which the leaflets are born are of small diameter which gives the foliage an attractive pendulant, drooping or "hanging down" appearance. The foliage of the new variety exhibits a striking purple color in the fall, principally in the month of October in Urbana, Ill.

A primary object of the invention is to provide a new and distinct white ash variety having the desirable characteristics referred to above and to be described in detail below.

Other objects and advantages of the invention will become apparent from the following detailed description when taken in conjunction with the accompanying illustrations in which:

FIG. 1 is a drawing of the new variety after about ten growing seasons, illustrating the dense broad growing habit and the pendulant effect of the leaflets; and FIG. 2 is an illustration of the leaflets bearing the purple fall color.

The new variety of white ash is characterized by the aforementioned broad dense growing habit, as distinguished from an upright ascending and open growth form. The leaves during the summer season are a darker green than other white ash observed in the area, and such leaves assume an outstanding purple fall color which persists until heavy frosts cause leaf drop. The small diameter rachis bearing the leaflets produces the pendulant effect referred to hereinabove. The male flower characteristics are observed with no seed production.

The new variety has been propagated by budding, and the new tree plants holds its distinguishing characteristics. References to colors in the following description are based on the Munsell Book of Color, Munsell Color Company, Inc., Baltimore, Md. (1929).

The distinguishing characteristics of the tree include dense, upright spreading, somewhat slower growth. The tree has male characteristics. The trunk is dark brown or gray with mainy close ridges crossing to form a diamond pattern. The branches are stout, glabrous; and the color of the branches is a glossy olive green, No. 137A. The lenticels or the branches are pale and prominent.

The tree assumes a height of about 18 ft. after about 10 growing seasons.

The foliage is described in association with its leaves, leaflets, flower buds and flowers.

LEAVES

The leaves are compound pinnate, and range from 20–25 cm. in length and from 14–28 cm. in width. Leaflets range in number from 7–9, usually 9. The rachis is of smaller diameter than other white ash observed in the area.

LEAFLETS

The leaflets are of medium size, having a length from 6–10 cm. and a width from 3–4.5 cm. The shape of the leaflets is ovate. The apex of the leaf is taper pointed, and the base is rounded to slightly cuneate. The margins of the leaflets are slightly dentate toward the apex, and are essentially entire toward the base. The color of the leaflets is dark green above, No. 147A; and dull pale green beneath, No. 147C. The leaflets change in autumn to greyed-purple, No. 197A. They are glabrous above, and essentially hairless beneath. The petioles are from 3–7 mm. long, and are glabrous.

FLOWER BUDS

There is a heavy bearing of flower buds noted each spring.

FLOWERS

Representative samples taken from several parts of the tree show the flowers to exhibit only male characteristics.

What is claimed is:

1. A new and distinct variety of white ash substantially as described and illustrated herein, characterized particularly by the unique combination of dense, broad, growing habit, dark green leaves of smaller size with small diameter petioles creating a drooping or pendulant character of the leaflets, and which leaflets turn to an attractive purple color in the autumn of the year, and with flowers exhibiting male characteristics.

No references cited.

ROBERT E. BAGWILL, Primary Examiner